(12) United States Patent
Sebok et al.

(10) Patent No.: US 7,019,834 B2
(45) Date of Patent: Mar. 28, 2006

(54) TRIBOLOGICAL DEBRIS ANALYSIS SYSTEM

(75) Inventors: Thomas J. Sebok, Tallmadge, OH (US); Dale R. Sebok, Tallmadge, OH (US); Joseph P. Kolp, North Canton, OH (US)

(73) Assignee: Lockheed Martin Corporation, Akron, OH (US)

( * ) Notice: Subject to any disclaimer, the term of this patent is extended or adjusted under 35 U.S.C. 154(b) by 438 days.

(21) Appl. No.: 10/162,380

(22) Filed: Jun. 4, 2002

(65) Prior Publication Data

US 2003/0223061 A1  Dec. 4, 2003

(51) Int. Cl.
*G01N 15/02* (2006.01)
*G06K 9/62* (2006.01)

(52) U.S. Cl. ............ 356/335; 382/199; 382/224; 382/225

(58) Field of Classification Search ............... 356/335, 356/336, 337, 338, 342, 343, 246
See application file for complete search history.

(56) References Cited

U.S. PATENT DOCUMENTS

| | | | |
|---|---|---|---|
| 3,198,064 A | 8/1965 | Moore | 88/14 |
| 3,947,121 A | 3/1976 | Cotter et al. | 356/38 |
| 4,393,466 A | 7/1983 | Deindoerfer et al. | 364/415 |
| 4,582,684 A | 4/1986 | Vogel et al. | 422/57 |
| 4,804,267 A | 2/1989 | Greenfield | 356/335 |
| 4,807,267 A | 2/1989 | Rifu et al. | 378/7 |
| 5,030,421 A | 7/1991 | Muller | 422/102 |
| 5,098,661 A | 3/1992 | Froehlich et al. | 422/102 |
| 5,241,189 A | 8/1993 | Vandagriff et al. | 250/575 |
| 5,449,622 A * | 9/1995 | Yabe et al. | 436/63 |
| 5,471,299 A * | 11/1995 | Kaye et al. | 356/336 |
| 5,572,320 A | 11/1996 | Reintjes et al. | 356/335 |
| 5,594,544 A | 1/1997 | Horiuchi et al. | 356/73 |
| 5,721,433 A * | 2/1998 | Kosaka | 250/573 |
| 5,766,957 A | 6/1998 | Robinson et al. | 436/165 |
| 5,780,865 A | 7/1998 | Miura et al. | 250/573 |
| 5,786,894 A * | 7/1998 | Shields et al. | 356/338 |
| 5,883,721 A | 3/1999 | Gilby et al. | 356/440 |
| 5,911,002 A * | 6/1999 | Mitsuyama et al. | 382/158 |

FOREIGN PATENT DOCUMENTS

| | | |
|---|---|---|
| EP | 0 556 971 A3 | 2/1993 |
| EP | 0644 414 A3 | 8/1994 |

(Continued)

OTHER PUBLICATIONS

Search Report UK Patent Office dated Sep. 9, 2002.

*Primary Examiner*—Gregory J. Toatley, Jr.
*Assistant Examiner*—Roy M. Punnoose
(74) *Attorney, Agent, or Firm*—Renner Kenner Greive Bobak Taylor & Weber

(57) ABSTRACT

A tribological debris analysis system includes a general purpose computer; and a tribological sensor system for generating data. The sensor system includes an optical flow cell a pump for pumping a fluid through the optical flow cell, a laser for illuminating the fluid flowing through the optical flow cell, and an imaging device for detecting any debris in the fluid illuminated by the laser. The imaging device sends the object information—in either the form of object elements or objection segments—representative of the debris to the general purpose computer for analysis. The general purpose computer classifies the debris according to size, any trends associated with the size of the debris, generating shape features of the imaged debris and identifying a type of object wear based upon the shape features.

14 Claims, 6 Drawing Sheets

FOREIGN PATENT DOCUMENTS

| | | |
|---|---|---|
| EP | 1245 945 A2 | 3/2002 |
| GB | 2 116 704 A | 1/1979 |
| GB | 2378 526 A | 2/2003 |
| JP | 62-112034 | 5/1987 |
| JP | 218417 | 8/1995 |
| WO | WO 95/12118 | 5/1995 |

* cited by examiner

TRIBOLOGICAL DEBRIS ANALYSIS SYSTEM

TECHNICAL FIELD

The present invention relates generally to fluid inspection systems. More particularly, the invention relates to a system to ensure accurate imaging of debris viewed through an optical flow cell. Specifically, the invention relates to a system that controls various components in the system and the exchange of data between those components.

BACKGROUND ART

It is known to provide fluid sampling devices using optical near-field imaging as disclosed in U.S. Pat. No. 5,572,320, which is incorporated herein by reference. Such a device is employed to determine the quantity, size, characteristics, and types of particulate matter in fluids. Examples of fluids which are monitored in such a system are lubricating oils used in engines and rotating machinery; hydraulic fluid used in various machinery; and fluids used in industrial quality control, food processing, medical analysis, and environment control. In its most common use, such a device monitors engine oil for metal particulates or flakes, wherein a size, number, and shape of particulates correspond to an engine condition and can alert one to particular problems with the engine. Non-metallic debris in the fluid can also be detected, such as fibers, sand, dirt and rust particles. Predicting failure is critically important in aircraft engines to avoid accidents and loss of life.

The early stages of engine wear cause small particulate matter, of about 50 microns or less in size, to be generated. These particulates have characteristic shapes indicative of the type of wear produced by specific wear mechanisms. As the wear process progresses, the amount and size of particulates increase. Accordingly, imaging and identifying smaller particles allows early identification of faults, thus, allowing more time for corrective maintenance and preventing unexpected catastrophic failures.

The advantage of the aforementioned system over previous systems is readily apparent when one considers that the previous systems only measured the amount of light passing through the material-laden oil, but gave no consideration as to the particular shape of the material. As best seen in FIGS. 1A–G, the various types of images rendered by a known system can provide a clear indication of the types of problems that are likely to occur based upon the shape and structure of the debris monitored. For example, in FIG. 1A, sliding wear particles are shown and these particles are believed to be caused by metal-to-metal contact due to overloading, misalignment, high speed and/or low oil viscosity. The debris shown in FIG. 1B represents fatigue wear particles which are gear or bearing pieces generated due to surface stress factors such as excessive load, contamination, and the like. FIG. 1C shows cutting wear particles that are generated by surface gouging, two body cutting due to break-in, misalignment, and three body cutting due to particle abrasion. FIG. 1D shows oxide particles which are caused by contamination, and red oxide caused by water or insufficient lubrication of the subject machinery.

It will also be appreciated that certain elements may be in the oil that generate false readings. These elements are classified and may be disregarded by the imaging system. For example, as shown in FIG. 1E, fibers are shown which are normally occurring or may be caused by improper sample handling. In particular, fibers can be from mishandling the fluid which generate false readings. But, valid readings of fibers may be indicative of problems in the system. For example, a filter or composite bearing may be disintegrating. In any event, occurrences of fibers are monitored. Instrument problems due to incomplete removal of air bubbles are represented in FIG. 1F. Finally, FIG. 1G shows flow lines which are a result of instrument problems caused by insufficient replacement of a new sample.

Known tribological debris analysis systems consist of a fluid sample that is connected to a pumping device. The pump is actuated and the fluid is drawn through an optical flow cell which is illuminated by laser light. A discrete input/output board connected to a dedicated computer system controls operation of the pump and the laser in a coordinated manner. An analog camera positioned opposite the laser light obtains an analog video image of particles passing through the optical flow cell. The dedicated computer system processes the analog video by sending the video signal to a digitizer which converts the signal to a digital image. The computer system processes the digital image to determine the shape and size of the particles rendered by the system. About ninety percent of the computer system's processing time is dedicated to pixel level processing associated with the analysis of an image and the detection of object elements. Accordingly, the system requires that the raw video input be directly sent to the general purpose computer for processing and analyzing of the images. It has been found that the known system is quite expensive and easily overloaded. Since the computer system is a dedicated device, it is limited in its ability to analyze the particles and detect any trends associated with the particles. Moreover, the known computer system is unable to check the lifetime history of a particular device when periodic samples are taken from the device. Therefore, such prior art systems, although effective, are not easily adapted for large scale use and implementation.

SUMMARY OF THE INVENTION

It is thus an object of the present invention to provide a tribological debris analysis system.

The foregoing and other objects of the present invention, which shall become apparent as the detailed description proceeds, are achieved by tribological debris analysis system, comprising a general purpose computer; and a tribological sensor system for generating data, the sensor system comprising an optical flow cell; a pump for pumping a fluid through the optical flow cell; a laser for illuminating the fluid flowing through the optical flow cell; and an imaging device for detecting debris in the fluid illuminated by the laser, and generating object segments representative of the debris and sending the object segments to the general purpose computer for analysis.

Other aspects of the present invention are attained by a tribological sensor system for imaging particles in a fluid comprising a fluid illumination delivery system for placing the fluid in a field of view; and an imaging device for detecting any particles in the field of view and generating object information representative of the particles for analysis.

Still other aspects of the present invention are attained by a computerized method for classifying particles in a fluid taken from a device, wherein the particle-containing fluid is imaged into object segments, the computerized method comprising receiving the plurality of object segments; generating a plurality of object elements from the plurality of object segments; and classifying the plurality of object elements according to predetermined characteristics.

It is another aspect of the present invention to provide a computerized method for classifying particles in a fluid taken from a device, wherein the particle-containing fluid is imaged into object information, the computerized method comprising: classifying the object information according to predetermined characteristics.

These and other objects of the present invention, as well as the advantages thereof over existing prior art forms, which will become apparent from the description to follow, are accomplished by the improvements hereinafter described and claimed.

BRIEF DESCRIPTION OF THE DRAWINGS

For a complete understanding of the objects, techniques and structure of the invention, reference should be made to the following detailed description and accompanying drawings, wherein.

BEST MODE FOR CARRYING OUT THE INVENTION

Figure 1A:
FIGS. 1A–G are examples of different types of particles detected by an optical debris analysis system according to the present invention.
Figure 1B:
Figure 1C:
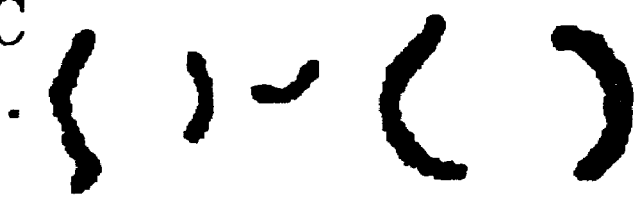
Figure 1D:
Figure 1E:
Figure 1F:
Figure 1G:
Figure 2:
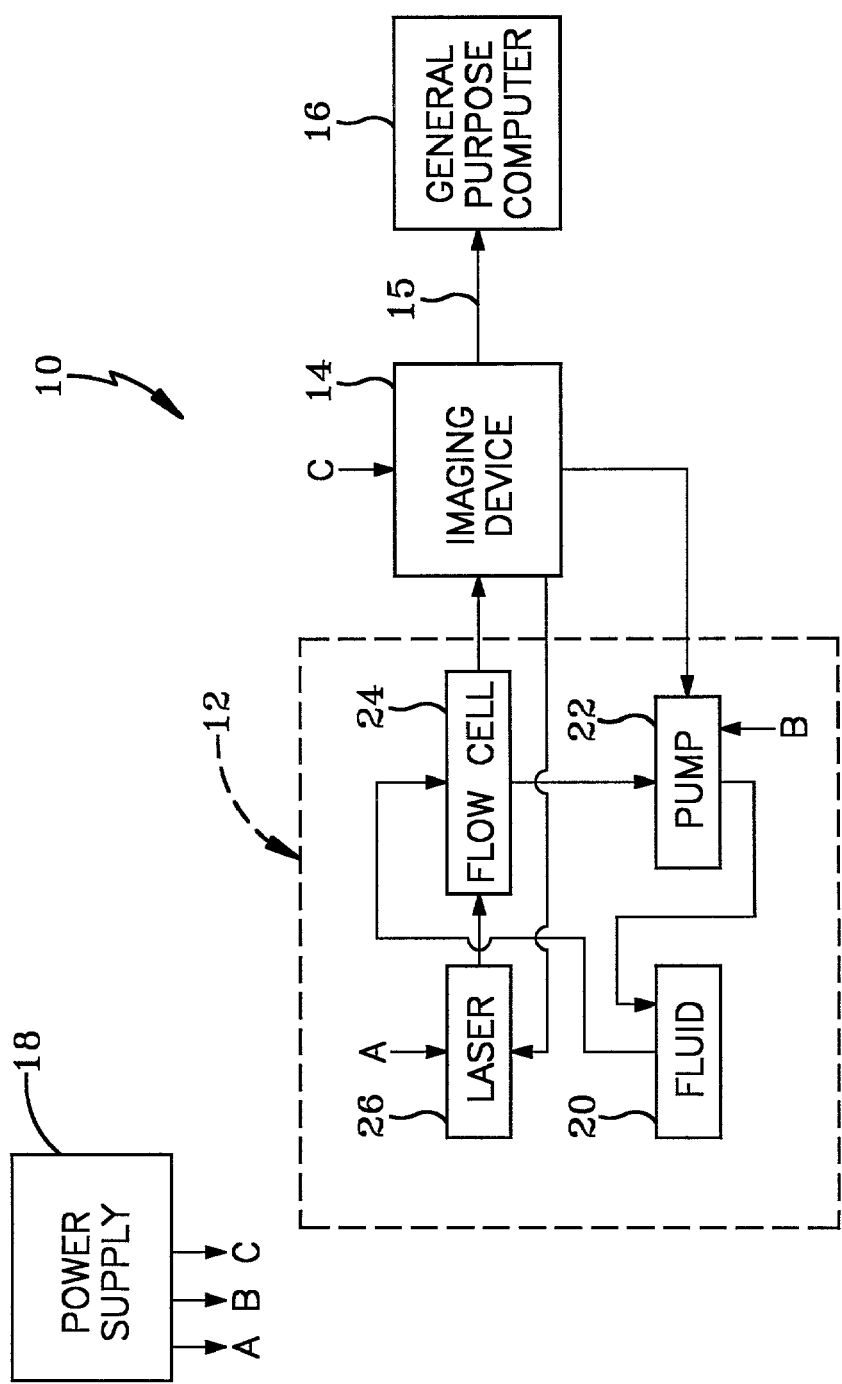
FIG. 2 is a schematic diagram of the system according to the present invention.

Referring now to the drawings and, more particularly to FIG. 2, a tribological debris analysis system according to the present invention is designated generally by the numeral 10. The system 10 includes an illumination delivery system 12 and an imaging device 14 which generates a data signal 15 received by a general purpose computer 16. A power supply 18 supplies power to the particular components of the system 10. Although a general purpose computer 16 may be used in the preferred embodiment it will be appreciated that most any computing device with the necessary memory, hardware and software could be utilized in the system 10. In all likelihood, the general purpose computer 16 is powered separately.

The illumination delivery system 12 includes a fluid container 20 for holding the fluid material to be analyzed. The fluid may be a lubricating oil used in engines and rotating machinery; hydraulic fluid used in various machinery; and fluids used in industrial quality control, food processing, medical analysis, and environmental control. Typically, the fluid sample is taken from and identified with a particular unit or device and if the device has multiple ports that particular port is identified. This information is input into the general purpose computer for cataloging purposes. In any event, the fluid container 20 is connected to a pump 22 which draws the fluid in the container through an optical flow cell 24. As the fluid is being drawn through the flow cell 24 a laser 26 illuminates one side of the flow cell 24 to generate an image that is detected by the imaging device 14. After the appropriate processing of the image, the imaging device 14 generates a data signal 15 that is received by the general purpose computer 16.

Figure 3:
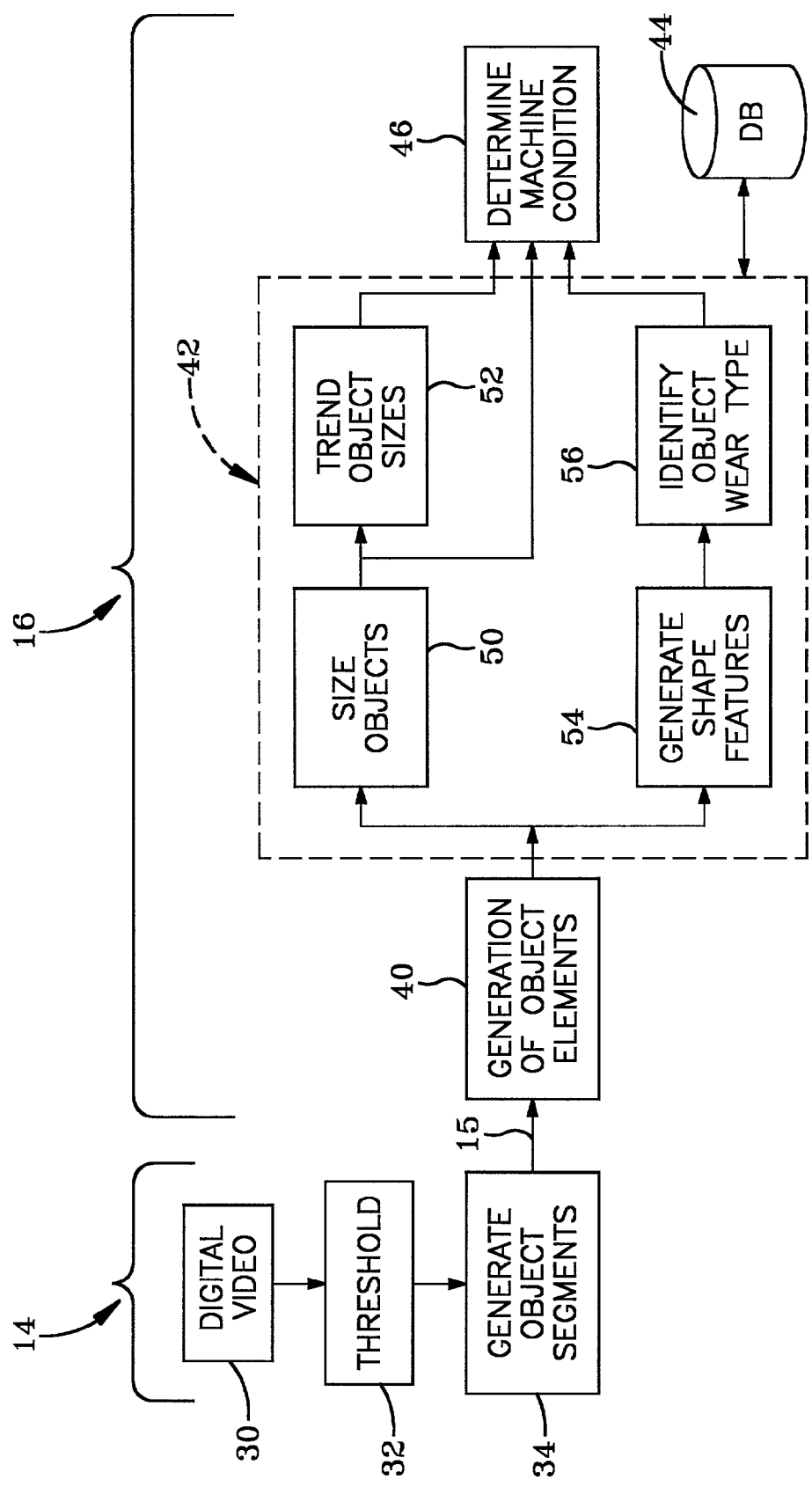
FIG. 3 is a processing flow chart showing functions of an imaging device and a general purpose computer according to the present invention.

Referring now to FIG. 3, a flow chart describing the general operational features of the system 10 is shown. The imaging device 14 generates a digital video signal at step 30. Initially, when the fluid begins flowing through the optical flow cell, an illumination map is generated. In the preferred embodiment, the illumination map comprises the first 32 frames of video to establish a base line illumination pattern. This allows the system to take into account the characteristics of the laser beam, which is circularly polarized light, and other artifacts associated with the system. And since various types of fluid material with different opacities are likely to be tested it is important to establish a base line level of illumination for analysis of the particles contained within the fluid.

After generation of the illumination map, the system performs a thresholding step 32. The digital video signal is initially provided at 256 levels of gray corresponding to the illumination map. The threshold step converts the 256 different levels of illumination to a bi-level image. In other words, if a particular pixel is deemed to have an intensity value in the lighter half of the 256 levels then it is designated as being an 'off' pixel. But, if the pixel is in the darker half of the spectrum then the pixel is deemed to be associated with an object and it is designated as an 'on' or darkened pixel. The thresholding process determines whether each pixel should be designated as part of an object or not. It will also be appreciated that the thresholding step could be further defined as four levels—instead of two—or however many levels are appropriate depending on the base thresholding level.

After completion of thresholding step 32, the thresholded information is used to generate object segments at step 34. An object segment is a contiguous group of pixels in a row wherein all pixels in the group have the 'not off' value. In other words, the object segments are individual rows of an object detected which are defined by a row number, a column start position, and a column stop position. The object segments are included in the data 15 that is sent to the general purpose computer 16.

The general purpose computer 16 receives the object segments in the data 15 and generates a set of object elements at step 40. It will be appreciated that the object elements are configured object segments which have some continuity between adjacent rows of pixels. Formation of the object elements may also be configured by filtering routines as deemed appropriate or based upon the past history of particles detected. In any event, after the generation of the object elements they are classified at step 42 according to different types of particles or debris as discussed in the description of FIGS. 1A–G. Upon completion of the classifying step, the general purpose computer at step 44 may access a hierarchical database 44 for comparing known types of particles with those particles detected in the fluid. Finally, at step 46, based upon the comparison of the particles and other features, a machine condition is determined. The computer 16 may use neural networks or other algorithms to classify the particles. This information is displayed by the general purpose computer with recommendations and/or information for the purpose of determining the wear conditions of the machinery from which the fluid was obtained. And if fluid is drawn from several different ports of the machinery this information can also be correlated and stored.

The classifying step 42 includes the steps of sizing the objects detected at step 50 which correlates to the expected useful life of the machinery from which the fluid was drawn. The size of the objects may be input directly to step 46 to determine the machine condition. In addition, the object sizes are input to process step 52 to determine the trend of the object sizes. In other words, at step 52 if there is an increase in object size or a decrease in object size this information can be detected and monitored. The trending in object sizes may also be used to analyze previous fluid samples taken from a particular port of a machine or used to compare similar machines to one another. At step 54, the general purpose computer may utilize the object elements to generate shape features which are indicative of the type of wear being experienced by the machine from which the fluid sample was drawn. This information is utilized at step 56 to identify the object wear type by comparing the shape features to those in the database. This information can be further utilized to determine the machine condition at step 46.

Figure 4:
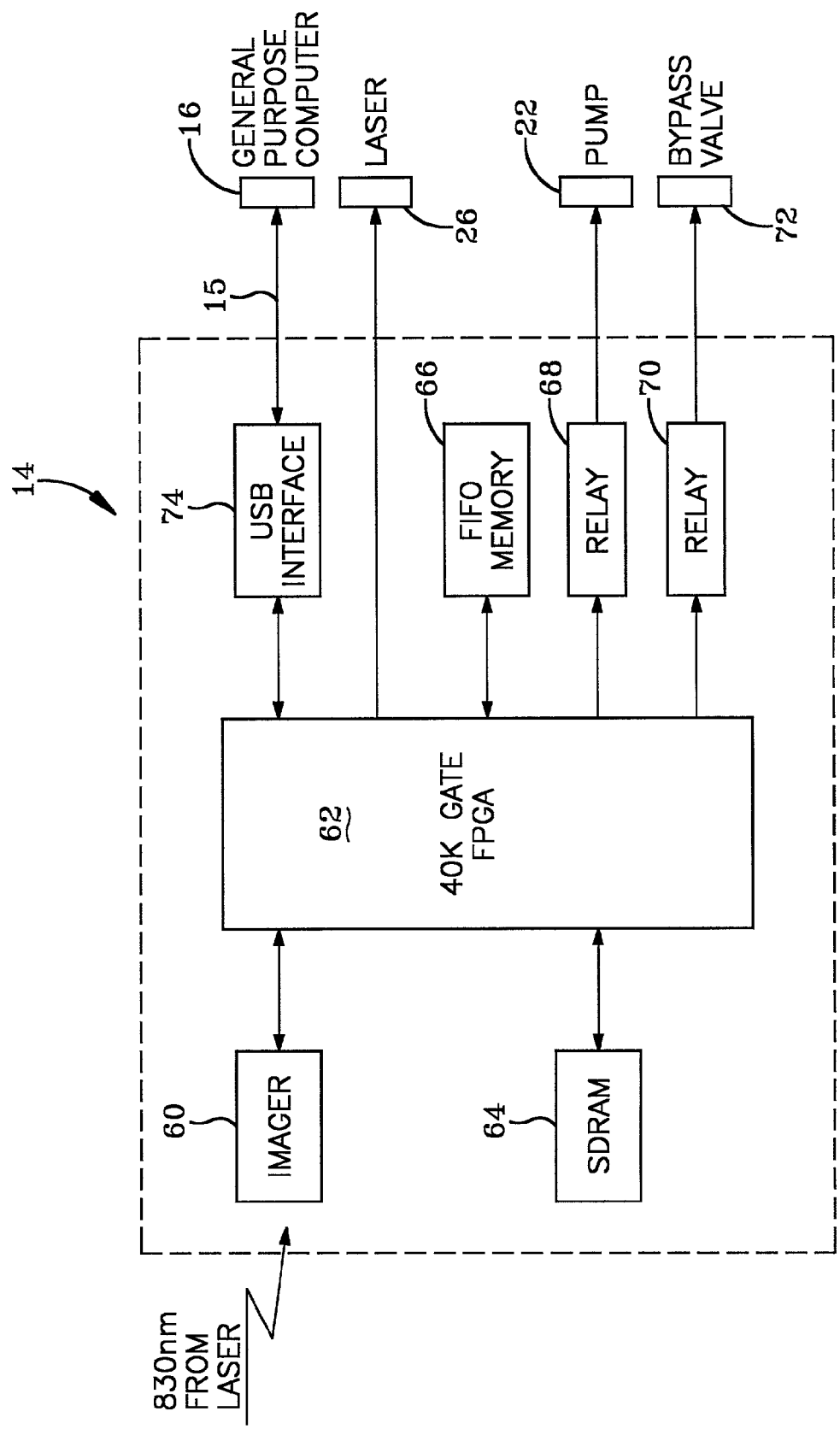
FIG. 4 is a block diagram of the imaging device according to the present invention.

Referring now to FIG. 4, the circuitry of the imaging device 14 will now be discussed. Light from the laser is projected at 830 nm through the flow cell onto a CMOS imager 60 which is 640×480 pixels and that operates at an update rate of 30 hz. The imager 60, which may also be referred to as a camera, generates a digital video signal of the laser-illuminated fluid sample. This information is transferred to a field programmable gate array 62 which performs the pixel processing, image filtering, image thresholding, segment detection and generation of global image statistics. Additionally, the array 62 functions to control the other components of the imaging device. These components include an interface device 74, which in the preferred embodiment is a universal serial bus (USB), the imager 60, the memory devices contained within the imaging device 14, the pump 22 and the laser 26. The USB interface 74 sends the object segment to the general purpose computer and receives instructions back from the general purpose computer. The array 62 also controls relays 68 that control the directional flow of the fluid through the pump 22 and a relay 70 that controls a bypass valve 72 which is utilized to "prime" the pump 22 prior to imaging any fluid flowing through the optical flow cell 24. In communication with the array 62 is a synchronous dynamic random access memory (SDRAM) device which is utilized to store the illumination map needed for thresholding the video signal. The SDRAM is a 16 by 1 megabyte memory device. Of course, it will be appreciated that any appropriately sized memory device could be implemented in the present invention. Another memory device associated with the imaging device 14 is a first-in first-out (FIFO) memory device 66 used to store the data processed by the array 62 until the general purpose computer 16 is in need of it.

Figure 5:
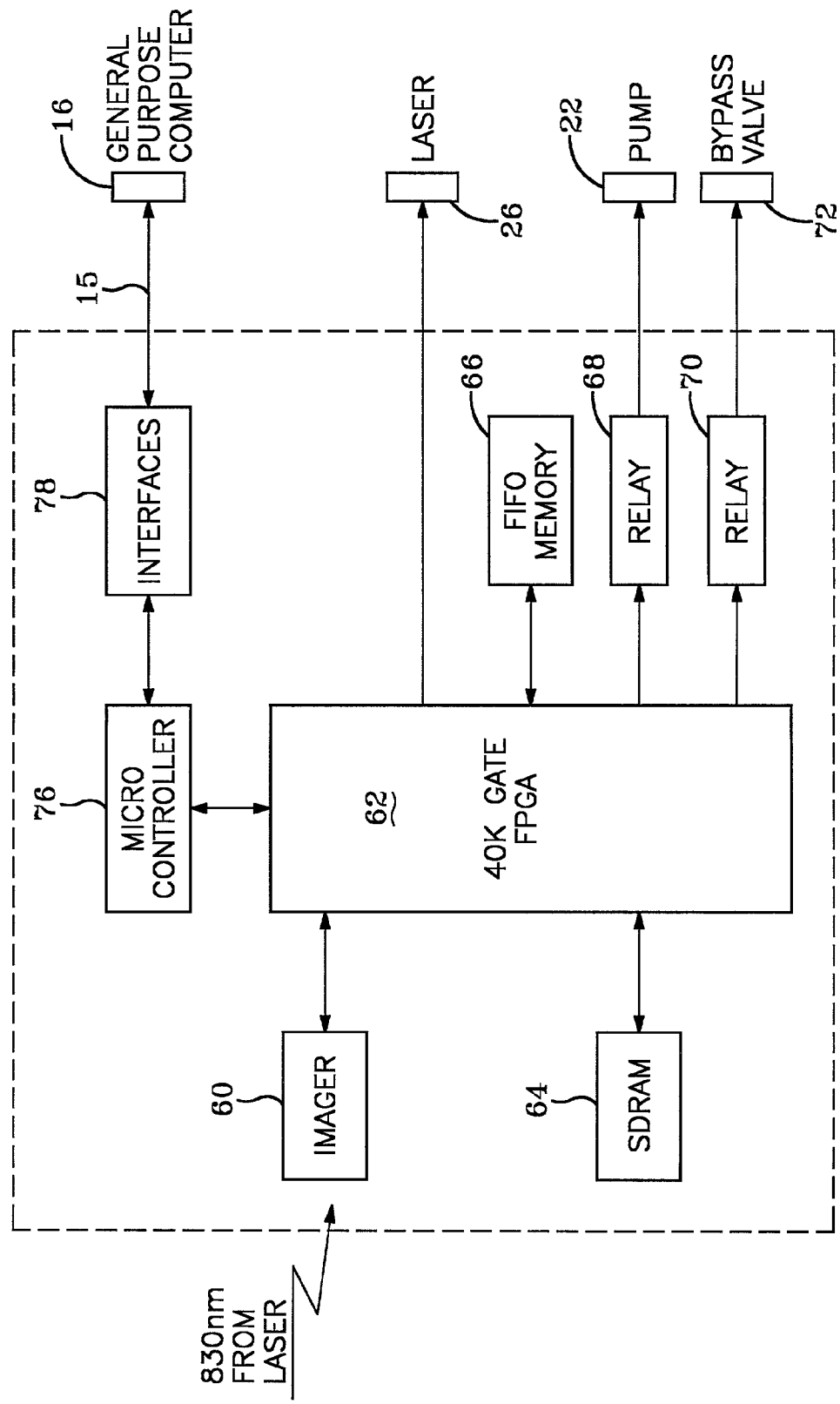
FIG. 5 is a block diagram of an alternative embodiment of the imaging device according to the present invention.

An alternative embodiment of the imaging device 14 is shown in FIG. 5. This device operates in much the same manner as the device shown in FIG. 4, but in this instance the imager 60 may be provided with a faster updating frequency. And in this embodiment a microcontroller 76 may be in communication with the array 62 to allow for different types of interface devices 78 to be in communication with the general purpose computer 16. The microcontroller 76 controls the interfaces and may take on additional object processing chores which allows for the detected segments to be converted into the object elements in the imaging device instead of by the general purpose computer. In any event, the object information transmitted to the general purpose computer will be object elements instead of object segments resulting in a further reduction in the required bandwidth and further enabling the user to use a less expensive general purpose computer or to more easily send the serial data to an appropriate computing device.

Figure 6:
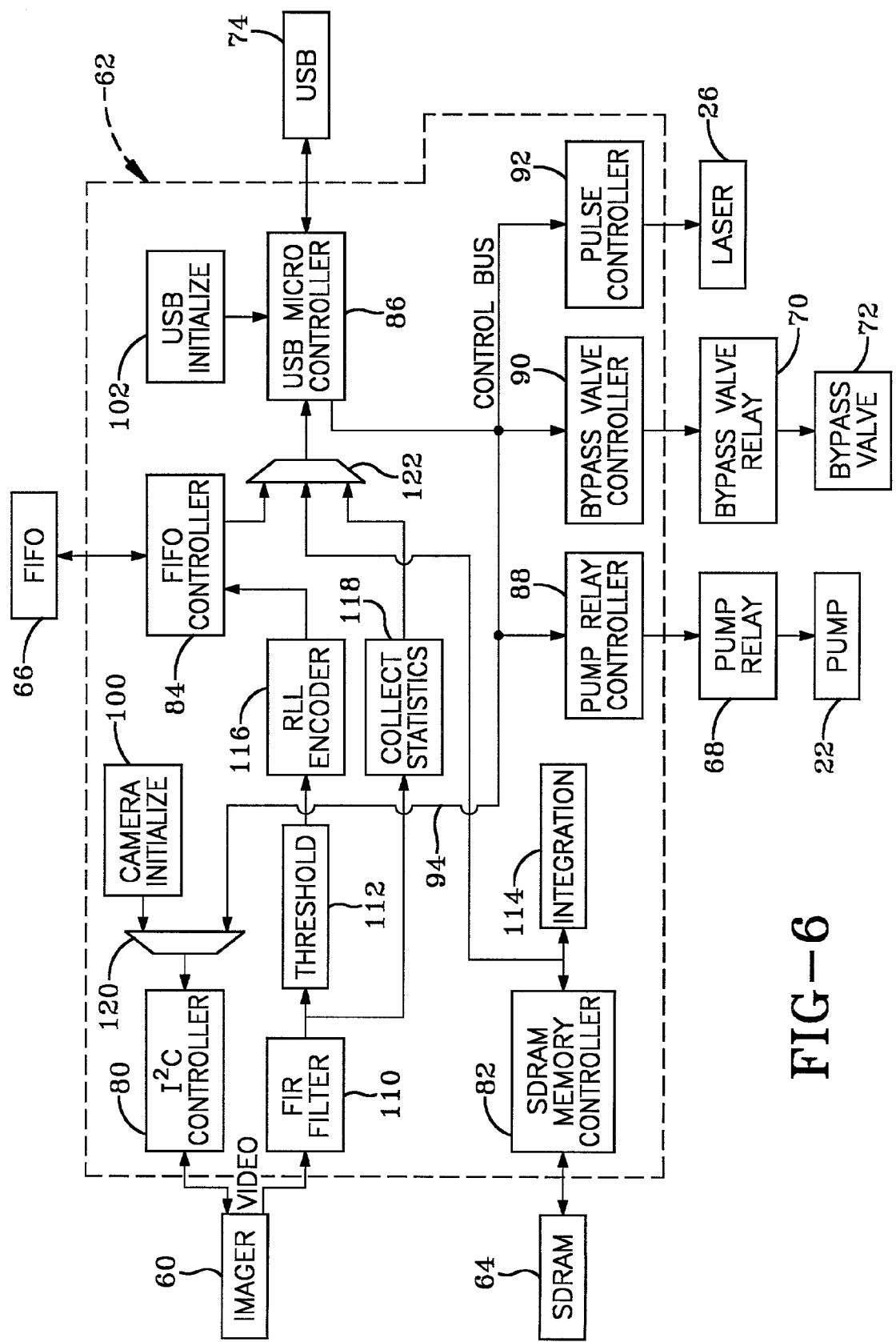
FIG. 6 is a block diagram of a field programmable gate array utilized by the system of the present invention.

Referring now to FIG. 6 a detailed schematic diagram of the array 62 is shown. As noted previously, the array 62 is in communication with the imager device 60 and memory devices 64 and 66. Output devices connected to the array include the general purpose computer 16 via the data signal 15, the pump 22, the bypass valve 72 and the laser 26. The array 62 includes a series of controllers which are utilized to control various aspects of these components that are connected to the array. In particular, the individual controllers include but are not limited to an I²C controller 80 which generates the necessary protocol to allow the programming and operation of the CMOS imager 60. Also provided is a SDRAM controller 82 which provides the necessary circuitry to provide the appropriate signals to control the operation of the SDRAM memory chip 64. Likewise, an FIFO controller 84 is responsible for controlling the operation of the first-in first-out memory 66 used to store objects segments until the computer 16 asks for them. A USB microcontroller 86 is responsible for controlling the USB interface 74 which organizes how data is sent to the general purpose computer. A pump relay controller 88, a bypass relay valve controller 90 and a pulse controller 92, which is associated with the laser 26, are also provided. The controllers 80, 86, 88, 90 and 92 are in communication with one another via a control bus 94

The array 62 may include initializing devices to facilitate the operation of the imaging device 14. In particular, a camera initializing device 100 sends appropriate signals to the I²C controller through a multiplexer 120 which also receives controller signals via the control bus 94. A second multiplexer 122 receives input signals from the FIFO controller 84 and the SDRAM memory controller 82. These signals are sent to the USB microcontroller 86 as deemed appropriate.

The array 62 may include a finite impulse response (FIR) filter used 110 to apply a high pass filter to the digital video signal. This filtered signal is then sent to a thresholding device 112 which converts the eight-bit gray level image into a bi-level image. The filtered signal is also sent to a collect statistics circuit 118 which examines the digital video stream coming in and determines the average intensity value for each frame of video. Additionally, the collect statistics circuit 118 determines the relative amount of video saturation present. The data from the circuit 118 is sent to the USB microcontroller 86 via the multiplexer 122 and is used by the general purpose computer 16 to implement an automatic gain control routine to properly set the laser pulse width and camera gain by the controller 92 for optimal lighting of the fluid under test. The thresholded video signal is sent by the thresholding device to a run length limited (RLL) encoder 116 which is responsible for detecting the object segments which are horizontally adjacent pixels in a row that the threshold device 112 has determined to be part of an object. Detected object elements are submitted to the FIFO memory device 66, and subsequently to the general purpose computer via the multiplexer 122.

Based upon the foregoing, the advantages of the present system are readily apparent. In particular, the present system allows for processing the digital video signal within the imaging device so as to allow for faster and more efficient processing of the images. In other words, it is now possible for the imaging device to generate 'object information'— object segments as shown in FIG. 4 or both object segments and object elements as shown in FIG. 5—that is then processed by the general purpose computer 16. The improvements discussed herein eliminate the need for a dedicated general purpose computer system to conduct all of the video image processing. Accordingly, the results can be displayed on most any off-the-shelf computing device while providing a system which is much less expensive. Additionally, the present device eliminates the need for a separate input/output board to control the general purpose computer and it removes the extra cabling and electronics needed to implement the previous system.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. A tribological debris analysis system comprising:
   a general purpose computer; and
   a tribological sensor system for placing a fluid in a field of view and generating data, said sensor system comprising:
   an optical flow cell;
   a fluid delivery system for delivering said fluid to said optical flow cell;
   a laser for illuminating the fluid flowing through said optical flow cell; and
   an imaging device for collecting imagery information of debris in the fluid illuminated by said laser and generating a digital video signal, said imaging device having an internal field programmable gate array for receiving said digital video signal and for processing said imagery information and generating object segments comprising a contiguous group of pixels in a row which are collectively representative of the debris, said field programmable gate array sending said object segments to said general purpose computer for analysis.

2. The system according to claim 1, wherein said field programmable gate array applies a threshold to said digital video signal to generate said object segments.

3. The system according to claim 2 wherein said object segments are converted into serial data.

4. The system accordingly to claim 1, wherein said general purpose computer comprises:
   a generating component for receiving said object segments and configuring said object segments into object elements which have continuity between adjacent rows of pixels;
   a classifying component for receiving and classifying said object elements according to predetermined characteristics; and
   an analyzing component for determining machine conditions based upon said classified object elements, wherein said classified object elements are associated with a type of wear.

5. The system according to claim 4, wherein said classifying component classifies said object elements according to shape, wear type, size and trends of element size.

6. The system according to claim 5, further comprising:
   a database component operative to maintain a database identifying wear properties of debris for comparison to said object elements by said classifying component.

7. The system according to claim 1, wherein said fluid delivery system comprises:
   a pump for pumping a fluid through said optical flow cell.

8. The system according to claim 1, wherein said imaging device comprises:
   a camera for generating an image from the field of view;
   wherein said field programmable gate array manipulates said image into object segments comprising a contiguous group of pixels in a row;
   at least one memory device connected to said field programmable gate array for storing said manipulated image; and
   an interface device connected to said field programmable gate array for exporting said manipulated image.

9. The system according to claim 8, wherein said field programmable gate array controls operation of said fluid delivery system, said laser, and said camera.

10. The system according to claim 9, wherein said sensor system further comprises:
    a bypass valve interposed between said fluid delivery system and said optical flow cell, said bypass valve facilitating the flow of fluid through said optical flow cell, said bypass valve controlled by said field programmable gate array.

11. The system according to claim 9, wherein said at least one memory device is a random access memory device in communication with said field programmable gate array to store an illumination map of a plurality of said images.

12. The system according to claim 9, wherein said at least one memory device is a first-in first-out memory device in communication with said field programmable gate array to store said object information for analysis.

13. The system according to claim 8, further comprising a microcontroller interposed between said interface device and said field programmable gate array for processing said manipulated image prior to exporting.

14. The system according to claim 1, wherein said sensor system further comprises:
    a microcontroller in communication with said field programmable gate array, said microcontroller configuring said object segments into object elements which have continuity between adjacent rows of pixels to reduce bandwidth transmission to said general purpose computer.

* * * * *